United States Patent [19]
Diefenbach et al.

[11] Patent Number: 5,302,733
[45] Date of Patent: Apr. 12, 1994

[54] PREPARATION OF METALLOCENES

[75] Inventors: Steven P. Diefenbach; Meng-Sheng Ao; John M. Power; Jamie R. Strickler, all of Baton Rouge, La.

[73] Assignee: Ethyl Corporation, Richmond, Va.

[21] Appl. No.: 860,339

[22] Filed: Mar. 30, 1992

[51] Int. Cl.$^5$ .......................... C07F 7/28; C07F 17/00
[52] U.S. Cl. ......................................... 556/11; 556/53
[58] Field of Search ................................... 556/11, 53

[56] References Cited

U.S. PATENT DOCUMENTS

| | | | |
|---|---|---|---|
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,036,034 | 7/1991 | Ewen | 502/117 |
| 5,071,808 | 12/1991 | Antberg et al. | 502/107 |
| 5,103,030 | 4/1992 | Rohrmann et al. | 556/12 |
| 5,145,819 | 9/1992 | Winter et al. | 502/117 |

FOREIGN PATENT DOCUMENTS

| | | | |
|---|---|---|---|
| 0320762 | 6/1989 | European Pat. Off. | 556/11 |
| 399348 | 11/1990 | European Pat. Off. | |
| 426643 | 5/1991 | European Pat. Off. | |

OTHER PUBLICATIONS

N. Klorsas und H. Köpf: Monatshefte fur Chemie 112, 887-897 (1981), Ring Substitued [1]-Titanocenophanes..

H. Köpf-N. Klouras Z. Naturforsch, Q3 .Z39 38b, 321-325 (1983) [1]Metallocenophanes: $^1$H-NMR Investigations.

Lawrence Summers, Robert H. Uloth and Ann Holmes, J.A.C.S.. vol. 77, pp. 3604-3606 (1955) Diaryl Bis-(cyclopentadienyl)-titanium Compounds.

Bajgur et al., Inorg. Chem. 1985, 24, 2539-2546 Synthesis Structural Characterization and Electrochemistry of [1] Metallocenophan Compexes, [Si(alkyl)$_2$(C$_5$H$_4$)$_2$]-MCl$_2$, M=Ti, Zr.

Hermann et al., Angen Chem. Int. Ed. Engl. 28 (1989) No. 11, pp. 1511-1512 The First Example of an Ethylene-Selective Soluble Ziegler Catalyst of the Zirconocene Class.

Jutzi et al., Chem. Ber. 119, 1750-1754 (1986) Metal Complexes with Bridged Permethylated Cyclopentadienyl Ligands.

Wild et al., J. of Organometallic Chem., 288 (1985) 63-67 ansa-Metallocene Derivatives.

Wilkinson et al., Communication to the Editor, J.A.C.S., Feb. 20, 1953, pp. 1011-1012 Bis-Cyclopentaddienyl Derivatives of Some Transition Elements.

Birmingham et al., Notes, J.A.C.S. Aug. 20, 1954, pp. 4179 A New Preparation of Bis-Cyclopentadienyl-Metal Compounds.

*Primary Examiner*—José G. Dees
*Assistant Examiner*—Porfirio Nazario
*Attorney, Agent, or Firm*—David M. Bunnell

[57] ABSTRACT

A racemic mixture of a chiral, silicon bridged transition metal metallocene, which is substantially free of meso isomer, is precipitated directly from a reaction mixture as it is formed by reacting an organic solvent solution of an alkali metal salt of a silicon bridged ligand with a transition metal tetrahalide-ether complex.

13 Claims, No Drawings

PREPARATION OF METALLOCENES

This invention relates generally to the preparation of metallocenes which are useful as catalyst components for olefin polymerization and more specifically to an improved process for forming high purity, racemic mixtures of silicon bridged metallocene catalysts of zirconium or titanium.

As is disclosed in European Patent Application 320,762, chiral stereorigid metallocene racemates together with a cocatalyst, such as an aluminoxane, are highly active catalysts for the production of stereospecific polymers The meso form of the metallocenes is not useful for this purpose The European Patent Application discloses a low temperature process −78° to 25° C., and preferably −40° to 0° C., to obtain a metallocene product solution, from which pure, crystalline racemic products are said to be obtained by combinations of filtration, extraction, evaporation and/or recrystallization steps. U.S. Pat. No. 5,017,714 discloses the preparation of silicon bridged metallocenes as oils from which the racemic and meso forms can be separated by various solvent extraction and/or crystallization steps. European Patent Application 426,643 discloses the preparation of metallocenes, which are stated to be of sufficient purity for subsequent use as a catalyst for the polymerization of olefins without further purification, by a solid-solid reaction of a transition metal salt and a powder of the solid reaction product of the ligand with an alkyllithium in a non-polar hydrocarbon liquid. A solid mixture of lithium salt and the metallocene are recovered.

We have now found a process which can be carried out at ambient to elevated temperatures to directly provide good yields of very pure racemic mixtures of metallocenes which are substantially free from the meso isomer and salt impurities. The metallocene racemates precipitate from the reaction and can be easily recovered by filtration. Any meso isomer or other impurities and, depending upon the solvent system used, all or most of the by-product alkali metal salt remain in the filtrate.

In accordance with this invention there is provided a process for making a racemic mixture of a chiral transition metal compound of the formula:

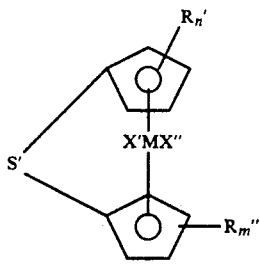

wherein
M is titanium or zirconium;
X' and X" are the same or different halogen;
n and m are the same or different integers from 1 to 4;
Each R' and R" are the same or different hydrocarbyl or silahydrocarbyl of 1–20 carbon atoms, and 0–2 silicon atoms, or taken together, two or more of R' or R" are hydrocarbylene or silahydrocarbylene of 1–20 carbon atoms and 0–2 silicon atoms; and
S' is a chain of 0–4 carbon atoms and 1–2 silicon atoms selected from the group consisting of silanylene, silaalkylene, oxasilanylene and oxasilaalkylene, in which each silicon atom is disubstituted with the same or different hydrocarbyl having 1 to 10 carbon atoms;
said compound being substantially free of meso isomer, said process comprising reacting in an organic solvent medium a solution of an alkali metal salt of a ligand having the formula:

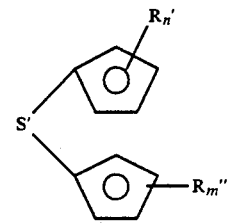

wherein S', R', R", m and n are as defined above, with a titanium or zirconium tetrahalide-ether complex in concentrations of said salt and said complex in the reaction mixture which are sufficient such that said chiral transition metal compound precipitates from said reaction mixture.

Examples of chiral transition metal compounds which are prepared in accordance with the process of the invention include, but are not limited to, racemic:

[1,1'-dimethylsilanylene-bis(3-methylcyclopentadienyl)]zirconium dichloride;

[1,1'-dimethylsilanylene-bis(indenyl)]zirconium dichloride;

[1,1'-dimethylsilanylene-bis(4,5,6,7-tetrahydroindenyl)]zirconium dichloride;

[1,1'-(1,1,2,2-tetramethyldisilanylene)-bis(3-methylcyclopentadienyl)]zirconium dichloride;

[1,1'-(1,1,2,2-tetramethyldisilanylene)-bis(4,5,6,7-tetrahydroindenyl)]zirconium dichloride;

[1,1'-dimethylsilanylene-bis(3-trimethylsilanylcyclopentadienyl)]zirconium dichloride;

1,1'-(1,1,2,2-tetramethyldisilanylene)-bis(3-trimethylsilanylcyclopentadienyl)]zirconium dichloride;

[1,1'-(1,1,3,3-tetramethyldisiloxanylene)-bis(4,5,6,7-tetrahydroindenyl)]zirconium dichloride;

[1,1'-(1,1,4,4-tetramethyl-1,4-disilanylbutylene)-bis(4,5,6,7-tetrahydroindenyl)]zirconium dichloride;

[1,1'-(2,2-dimethyl-2-silapropylene)-bis(3-methylcyclopentadienyl)]zirconium dichloride;

[1,1'-dimethylsilanylene-bis(3-methylcyclopentadienyl)]titanium dichloride;

[1,1'-dimethylsilanylene-bis(indenyl)]titanium dichloride;

[1,1'-dimethylsilanylene-bis(4,5,6,7-tetrahydroindenyl)]titanium dichloride;

[1,1'-(1,1,2,2-tetramethyldisilanylene)-bis(3-methylcyclopentadienyl)]titanium dichloride;

[1,1'-(1,1,2,2-tetramethyldisilanylene)bis(4,5,6,7-tetrahydroindenyl)]titanium dichloride;

[1,1'-dimethylsilanylene-bis(3-trimethylsilanylcyclopentadienyl)]titanium dichloride;

[1,1'-(1,1,2,2-tetramethyldisilanylene)-bis(3-trimethylsilanylcyclopentadienyl)]titanium dichloride;

[1,1'-(1,1,3,3-tetramethyldisiloxanylene)-bis(4,5,6,7-tetrahydroindenyl)]titanium dichloride;

[1,1'-(1,1,4,4-tetramethyl-1,4-disilanylbutylene)-bis(4,5,6,7-tetrahydroindenyl)]titanium dichloride;

[1,1'-(2,2-dimethyl-2-silapropylene)-bis(3-methylcyclopentadienyl)]titanium dichloride.

The ligand salts can be prepared by known alkylation/silylation steps. Alkali metal alkyls and, preferably, alkyl and aryllithium compounds are used in the alkylation/silylation steps. For example, indene or cyclopentadiene are reacted with alkyllithium such as methyllithium or butyllithium, in a suitable solvent, and preferably an ether such as diethyl ether, tetrahydrofuran, or mono-,di-, tri- or tetraglyme to form the corresponding lithium indenide or cyclopentadienide. If an alkylated ligand is desired, the lithium compound can then be reacted with a corresponding alkylhalide to yield the alkylated ligand. For example, n-butylchloride may be reacted with lithium indenide to yield n-butyl indene, and methylchloride with lithium cyclopentadienide to yield methylcyclopentadiene. Silylation may be accomplished in an analogous manner, such as by reacting lithium indenide, methylcyclopentadienide or trimethylsilanylcyclopentadienide, with dimethyldichlorosilane; or lithium indenide, methylcyclopentadienide or trimethylsilanylcyclopentadienide, with di(-chloromethyl) dimethylsilane. The bridge formation may also be completed before alkylation/silylation, as the order thereof is not generally critical.

Following formation of the desired silicon bridged ligand structure, the metallocene is formed by reaction of the di-lithium, di-potassium or di-sodium salt of the ligand with an organic solvent solution of the transition metal halide, for example, zirconium or titanium tetrachloride. Preferably, the ligand salt and the transition metal halide are reacted in about equimolar amounts, but, for example, amounts of from about 0.5 to 5 moles of salt per mole of transition metal halide can also be used.

The alkali metal salt of the ligand is preferably prepared in a primarily hydrocarbon medium by adding an alkali metal lower alkyl ($C_1$ to $C_6$) compound such as, for example, methyllithium, n-butyllithium, s-butyllithium, t-butyllithium, phenyllithium and the like contained in a hydrocarbon solvent such as, for example hexanes, cyclohexane, heptane, pentane, toluene and the like to an ether solution of the ligand in volume proportions of from about 0.5:1 to 20:1 hydrocarbon to ether solvent such that the alkali metal salt ether complex precipitates from the solution. This reaction can be run at temperatures of $-20°$ C. to 35° C. as extremely low temperatures are not required.

The solid alkali metal salt is then dissolved in a cyclic or acyclic ether such as, for example, diethyl ether, tetrahydrofuran, glymes (e.g. dimethoxyethane), di-n-butyl ether, dioxane, di-isopropyl ether and the like for reaction with the transition metal halide.

The transition metal halide is used in the form of an ether complex which can be prepared either in a hydrocarbon or halocarbon solvent and isolated from the reaction mixture or in a hydrocarbon solvent and used directly in the reaction with the ligand salt without separation from the solvent medium In fact, the presence of the hydrocarbon solvent in the ligand salt reaction improves the yield of metallocene product.

It is necessary that the reactants be used in concentrations, based on the total volume of organic solvent medium in the reaction mixture, which are sufficiently high to cause the metallocene product to precipitate from the reaction mixture as it forms. Concentrations of ligand salt of at least about 0.20 molar and, preferably from about 0.25 to 1 molar based on the total volume of solvent in the reaction are used. Similar concentrations of the transition metal halide are also used i.e. about 0.25 molar to 1 molar. We have, surprisingly, found that a very pure 99% racemic mixture precipitates from the reaction mixture and that the reaction can be run at ambient to elevated temperatures of about 65° C. without significant loss of yield. Reaction temperatures of from about $-20°$ C. to 55° C. are preferred and from about 25° C. to 50° C. are more preferred.

The solvent medium for the reaction can be an ether medium or preferably a mixture of ether and hydrocarbon solvent in proportions of up to about 0.45 (preferably about 0.1 to 0.4) parts by volume hydrocarbon per part by volume of ether solvent. Examples of suitable hydrocarbon solvents include but are not limited to hexanes, cyclohexane, heptane, pentane, toluene, benzene, cyclooctane, and the like. A further advantage of the process of the invention is that the metallocene can be recovered free or substantially free of alkali metal salt by-product which remains in the reaction mixture.

The invention is further illustrated by, but is not intended to be limited to, the following examples.

EXAMPLE 1

A. Preparation of Lithium Indenide

In a 500-mL flask were placed 32.62 g of technical grade indene (92.5 wt %) and 165 mL of diethyl ether. To this stirred solution were added 99.5 mL of 2.5 M n-BuLi (in hexanes) over 45 minutes. The reaction was exothermic and the solvent refluxed spontaneously and was returned to the reaction by an ice-water cooled condenser. A clear orange solution of lithium indenide was obtained.

B. Silylation of Lithium Indenide

The lithium indenide solution prepared according to procedure A was diluted with an additional 90 mL of ether and the cooled to 0° C. To this stirred solution were added 16.59 g of neat dichlorodimethylsilane over a 1 hour period. A white precipitate formed during the addition. After the addition was complete, the reaction was allowed to warm to ambient temperature. The lithium chloride precipitate was removed by filtration. The solids were washed with 53 mL of diethyl ether and the filtrates combined. The clear orange-yellow colored solution contained $(CH_3)_2Si(indenyl)_2$.

C. Preparation of $Li_2(CH_3)_2Si(indenide)_2 \cdot (Et_2O)$

To the solution of $(CH_3)_2Si(indenyl)_2$ prepared according to procedure B were added 99.8 mL of 2.5 M n-BuLi (in hexanes) over a 55 minute period. The solvent refluxed gently and was returned to the reaction with an ice-water cooled condenser. Off-white solids of product began precipitating midway through the addition. After all of the n-BuLi was added, the reaction was stirred for an additional two hours and then 87 grams of cyclohexane were added. The solids were then filtered and washed with an additional 85 g of cyclohexane. After drying the solids, the yield of pure $Li_2(CH_3)_2Si(indenide)_2 \cdot (Et_2O)$ was 33.0 g (67%).

D. Preparation of $ZrCl_4(THF)_2$

In a 3-L flask were placed 97.76 g of $ZrCl_4$ and 1500 mL of methylene chloride. The $ZrCl_4$ partially dissolved. To this stirred solution were added 62.5 g of THF over 2 hrs. After stirring for another 30 minutes, the solution was filtered through Celite and the clear orange-yellow solution was concentrated to 800 mL. White solids started to precipitate. The solution was further saturated by adding 700 mL of cyclohexane. The solution was cooled at −25° F. for over 3 hrs. and then the off-white precipitated solids were isolated by filtration and dried in vacuo. The yield of $ZrCl_4(THF)_2$ was 142.36 g (89.9%).

Preparation of rac-[1,1'-Dimethylsilanylene-bis(indenyl)]Zirconium Dichloride (LiCl free)

The $ZrCl_4(THF)_2$, prepared according to procedure D, was placed in a 2-L flask with 450 mL of THF. The salt partially L dissolved. A THF solution of $Li_2(CH_3)_2Si(indenide)_2.Et_2O$, prepared according to procedure C, (141.5 g in 900 mL of THF) was added dropwise to the slurry of $ZrCl_4(THF)_2$ over 10 hrs. Orange crystalline solids precipitated during the addition. After stirring overnight, the orange solids were filtered, washed with heptane and $Et_2O$, and dried in vacuo. The yield of orange solids was 79.91 g (47.3%). The solids were determined to contain >99% rac-[1,1'-dimethylsilanylene-bis-(indenyl)]zirconium dichloride (by $^1H$ NMR) and a negligible amount of LiCl by inductive coupled plasma (ICP).

EXAMPLE 2

Preparation of $ZrCl_4(THF)_2$ Slurry

In a 1-L flask were placed 25.95 g of $ZrCl_4$ and 110 mL of hexanes. To this stirred suspension of $ZrCl_4$ were added 70 mL of THF over 24 minutes. A maximum temperature of 40.4° C. was reached by the end of the addition. To this slurry were added an additional 130 mL of THF all at once. No rise in temperature occurred at this point. The slurry was then stirred for 20 minutes.

Preparation of rac-[1,1'-dimethylsilanylene-bis-(indenyl)]Zirconium Dichloride (mixed solvent/ambient temperature)

A THF solution (made by dissolving 41.63 g of $Li_2(CH_3)_2Si(indenide)_2.Et_2O$ in 138 mL of THF), was added dropwise to the slurry of $ZrCl_4 (THF)_2$ over 6 hrs. Orange solids precipitated throughout the addition. The solution was stirred overnight (17 hrs.) after the addition was completed. The solids were less sticky and more free-flowing after stirring overnight. The orange powder was filtered, washed with 95 mL of $Et_2O$, and dried thoroughly in vacuo. The yield of orange solids was 35.82 g. These solids contained >99% rac-[1,1'-dimethylsilanylene-bis-(indenyl)] zirconium dichloride (by $^1H$ NMR) and 4 wt. % LiCl (by ICP). The yield of pure product was 69%.

EXAMPLE 3

Preparation of $ZrCl_4(THF)_2$ Slurry

In a 500-ml flask were placed 15.10 g of $ZrCl_4$ and 62 mL of hexanes. To this stirred suspension of $ZrCl_4$ were added 40 mL of THF over 12 minutes. To this slurry was added an additional 75 mL of THF all at once.

Preparation of rac-[1,1'-Dimethylsilanylene-bis(indenyl)]Zirconium Dichloride (mixed solvent, elevated temperature)

The slurry of $ZrCl_4 (THF)_2$ prepared above was heated to approximately 50° C. in a water bath. A THF solution, made by dissolving 24.06 g of $Li_2(CH_3)_2Si(indenide)_2.(Et_2O)$ in 140 mL of THF, was added dropwise to the slurry of $ZrCl_4(THF)_2$ over 3 hrs. The reaction temperature was kept between 50°-54° C. over this time. The reaction initially separated into two phases and about midway through the addition the oil had completely dissipated and orange solids began to precipitate. After the addition was completed, the reaction was allowed to cool to ambient temperature. Most of the orange solids precipitated upon cooling to room temperature. After stirring overnight, the orange powder was filtered, washed with $Et_2O$, and dried thoroughly in vacuo. The yield of orange solids was 18.0 g. The chloroform soluble solids contained >99% rac-[1,1'-dimethylsilanylene-bis-(indenyl)]zirconium dichloride (by $^1H$ NMR). The orange solids contained 4.1% LiCl (by ICP). The yield of pure product was 60%.

Comparison

In a 6-dram vial were placed 1.0 g of $ZrCl_4$ and 1.6 g of $Li_2(CH_3)_2Si(indenide)_2.(Et_2O)$. Upon stirring the white solids, the mixture became pink within a few minutes. To this solid mixture were added 20 mL of $Et_2O$. An exothermic reaction ensued and orange solids formed. This reaction was stirred for one hour. The orange solids were filtered, washed with a few milliliters of $Et_2O$, and dried in vacuo. The yield of [1,1'-dimethylsilanylene-bis-(indenyl)]zirconium dichloride (and LiCl) was 2.03 g. By $^1H$ NMR, the product was determined to be a mixture of rac- (62%) and meso- (28%) isomers.

What is claimed is:

1. A process for making a racemic mixture of a chiral transition metal compound of the formula:

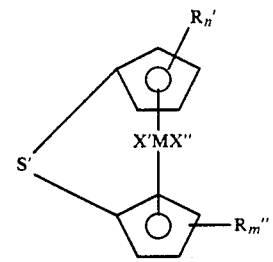

wherein;

M is titanium or zirconium;

X' and X" are the same or different halogen;

n and m are the same or different integers from 1 to 4;

each R' and R" are the same or different hydrocarbyl or silahydrocarbyl of 1-20 carbon atoms, and 0-2 silicon atoms, or taken together, two or more of R' or R" are hydrocarbylene or silahydrocarbylene of 1-20 carbon atoms and 0-2 silicon atoms; and S' is a chain of 0-4 carbon atoms and 1-2 silicon atoms selected from the group consisting of silyanylene, silaalkylene, oxasilanylene and oxasilaalkylene, in which each silicon atom is disubstituted with the same or different hydrocarbyl having 1 to 10 carbon atoms;

said compound being substantially free of meso isomer, said process comprising reacting, at a temperature of from about 25° to 65° C., in an organic solvent medium which includes a cyclic ether, a solution of an alkali metal salt of a ligand having the formula:

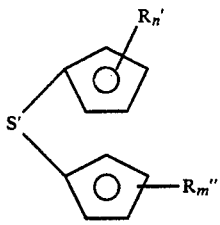

wherein S', R', R", m and n are as defined above, with a titanium or zirconium tetrahalide-ether complex in concentrations of said salt and said complex in the reaction mixture which are each from about 0.2 to 1 molar based on the total volume of organic solvent medium such that said racemic mixture of chiral transition metal compound precipitates from said reaction mixture.

2. A process according to claim 1 wherein the concentrations of said alkali metal salt and said complex in the reaction mixture are each from about 0.25 to 1 molar based on the total volume of organic solvent medium.

3. A process according to claim 1 wherein the molar portion of said alkali metal salt per mole of said complex is from about 0.5 to 5.

4. A process according to claim 3 wherein the reaction temperature is from about 25° to 55° C.

5. A process according to claim 2 wherein said alkali metal is lithium, S' is silanylene and said tetrahalide ether complex is a complex of zirconium.

6. A process according to claim 2 wherein said cyclic ether is tetrahydrofuran.

7. A process according to claim 2 wherein said solvent medium is a mixture of hydrocarbon and a cyclic ether in proportions of up to about 0.45 parts by volume hydrocarbon per part by volume ether.

8. A process according to claim 2 wherein said solution of alkali metal salt of said ligand is added to a slurry of said tetrahalide-ether complex in an organic solvent.

9. A process according to claim 8 wherein said precipitated racemic mixture of chiral transition metal compound contains less than about 1.0 percent of meso isomer.

10. A process according to claim 8 wherein said precipitated racemic mixture of chiral transition metal compound contains less than about 5 wt. percent alkali metal halide salt by-product.

11. The process of claim 1 wherein the tetrahalideether complex is a tetrahalide-tetrahydrofuran complex and said organic solvent medium comprises tetrahydrofuran.

12. The process of claim 2 wherein said organic solvent medium is tetrahydrofuran.

13. The process of claim 7 wherein said cyclic ether is tetrahydrofuran.

* * * * *